United States Patent
Sørensen et al.

(10) Patent No.: US 7,259,243 B2
(45) Date of Patent: Aug. 21, 2007

(54) PROCESS FOR ISOLATION OF OSTEOPONTIN FROM MILK

(75) Inventors: Esben Skipper Sørensen, Sabro (DK); Steen Ostersen, Herning (DK); Dereck Chatterton, Århus V (DK); Hans Henrick Holst, Videbæk (DK); Kristian Albertsen, Videbæk (DK)

(73) Assignee: Arla Foods Amba, Viby J (DK)

( * ) Notice: Subject to any disclaimer, the term of this patent is extended or adjusted under 35 U.S.C. 154(b) by 723 days.

(21) Appl. No.: 10/168,303

(22) PCT Filed: Jan. 4, 2001

(86) PCT No.: PCT/DK01/00005

§ 371 (c)(1),
(2), (4) Date: Nov. 12, 2002

(87) PCT Pub. No.: WO01/49741

PCT Pub. Date: Jul. 12, 2001

(65) Prior Publication Data

US 2003/0149249 A1    Aug. 7, 2003

(30) Foreign Application Priority Data

Jan. 7, 2000    (DK) ................. 2000 00013

(51) Int. Cl.
C07K 1/00    (2006.01)
C07K 14/00   (2006.01)
C07K 16/00   (2006.01)
C07K 17/00   (2006.01)

(52) U.S. Cl. ............ 530/351; 530/350; 530/412; 530/415; 530/418

(58) Field of Classification Search .......... None
See application file for complete search history.

(56) References Cited

FOREIGN PATENT DOCUMENTS

EP    0 404 425    12/1990

OTHER PUBLICATIONS

Kunz C and Lonnerdal B Human milk proteins: separation of whey proteins and their analysis by polyacrilymide gel electrophoresis, fast protein liquid chromatography (FPLC) gel filtration, and anion exchange chromatography. An J Clin Nut. 1989 (49):464-70.*

Bayless KJ, Davis GE, Meininger GA Isolation and Biological Properties of Osteopontin from Bovine Milk. Protein Expression and Purification. 1997.(9):309-314.*

Prince CW, Oosawa T, Butler WT, Tomana M, Bhown AS, Bhown M Schrohenloher RE Isolation, Characterization and Biosynthesis of a Phosphorylated Glycoprotein from Rat Bone. J Biol Chem (1987) 262:2900-2907.*

Sorensen ES, Petersen TE Purification and charaterization of three proteins isolated from the protease fraction of bovine milk. J Dairy Res (1993) 60:189-97. Abstract.*

Sorensen S., Justensen, S.J., Johnsen, A.H. Identification of a macromolecular crystal growth inhibitor in human urine as osteopontin. Urol Res (1995) 23(5):327-34 (abstract).*

Zhi Yong Ju et al., "Gelation of pH-aggregated Whey Protein Isolate Solution Induced by Heat, Protease, Calcium Salt, and Acidulant", *J. Agric. Food Chem.*, vol. 46, pp. 1830-1835, (1998).

Erdjan Salih et al., "Identification of the Phosphorylated Sites of Metabolically $^{32}$P-Labeled Osteopontin From Cultured Chicken Osteoblasts", *The Journal of Biological Chemistry*, vol. 272, No. 21, pp. 13966-13973, (May 1997).

Kayla Bayless et al., "Isolation and Biological Properties of Osteopontin From Bovine Milk", Abstract from Protein Expression and Purification, vol. 9, Database accession No. PREV199799513298, XP002146905, (Jul. 1997).

* cited by examiner

*Primary Examiner*—Eileen B. O'Hara
*Assistant Examiner*—Xiaozhen Xie
(74) *Attorney, Agent, or Firm*—Finnegan, Henderson, Farabow, Garrett, & Dunner L.L.P.

(57) ABSTRACT

A process for isolation of milk osteopontin from a material containing milk osteopontin by optionally mixing the milk material with a calcium source and separate the osteopontin containing phase from the rest of the milk material by pH adjustment.

20 Claims, No Drawings

PROCESS FOR ISOLATION OF OSTEOPONTIN FROM MILK

The present invention relates to a new process for isolation of osteopontin from milk.

Osteopontin (OPN) is a secreted adhesive glycophosphoprotein originally isolated from the collagenous extra cellular matrix of mineralized bone (Franzén A, Heinegård, D. 1985. Isolation and characterization of two sialoproteins present only in bone calcified matrix. Biochem. J. 232:715-724.). In the recent years, osteopontin has been found to be expressed by a number of different cell types including osteoblasts, arterial smooth muscle cells, leukocytes, several types of epithelial cells and transformed cells of different lineages (Denhardt D T, Butler W T, Chambers A F, Senger D R. (eds.). 1995. Osteopontin: role in cell signalling and adhesion. Ann. N.Y. Acad. Sci., 760). Accordingly, OPN has been detected in many tissues including kidney, placenta, secretory epithelia and ganglia of the inner ear, and smooth muscle of the vascular system (Butler W T, Ridall A L, McKee M D. 1996. Osteopontin. In Bilezekian J P, Rai L G, Rodan G A (eds.) Principles of bone biology. Academic Press, San Diego, Calif., U.S.A., pp. 167-181. Furthermore OPN is also present in many body fluids, notably plasma, urine, bile and milk, and it displays elevated expression in many transformed cells (Senger D R, Peruzzi C A, Gracey C F, Papadopoulos A, Tenen D G. 1988. Secreted phosphoproteins associated with neoplastic transformation: close homology with plasma proteins cleaved during blood coagulation. Cancer Res. 48: 5770-5774). Osteopontin is highly acidic with approximately 25% of the amino acid being aspartate/aspartic acid and glutamate/glutamic acid as well as a significant number of phosphorylated amino acids (Sørensen E S, Petersen T E. 1994 Identification of two phosphorylation motifs in bovine osteopontin. Biochem. Biophys. Res. Commun. 198:200-205; Sørensen, E S, Højrup, P, Petersen, T E. 1995. Posttranslational modifications of bovine osteopontin: Identification of twenty-eight phosphorylation and three O-glycosylation sites. Protein Sci. 4:2040-2049).

Osteopontin contains an RGD (arginine, glycine, aspartate) integrin-binding sequence, and it can promote attachment of cells to various surfaces, for example the attachment of osteoblasts to bone during bone remodelling. In addition to cell attachment capability, osteopontin can act as a cytokine. Other proposed uses or roles for osteopontin include chemotaxis and inhibition of nitric oxide synthase expression.

Thus, osteopontin has been proposed for use as a pharmaceutical agent. EP 705842 proposes the use of osteopontin in diagnosis, prophylaxis and therapy of osteoarthritis and rheumatiod arthritis. Osteopontin is also believed to play a role in enhancing bone growth and wound healing in mammals, cf. for example EP 942452 and WO 9933415. Further, osteopontin has been proposed for inhibition of nitric oxide, cf. U.S. Pat. No. 5,695,761. Osteopontin has also been proposed for solubilization of divalent metal ions for addition to foods, cf. abstract of JP 9173018.

Osteopontin has been isolated in research scale amounts (micrograms to low milligram's scale) from a number of tissues and fluids, including mineralized bone. However, there is a huge demand for osteopontin for experimental as well as for industrial use. All known processes for isolating osteopontin are at experimental scale giving too small amounts for industrial use.

Sørensen, E S, Petersen T. 1993. Journal of Dairy Research 60, 189-197, Purification and characterization of three proteins isolated from the proteose peptone fraction of bovine milk describes a method involving TCA, trichloro acetic acid, precipitation of proteins, This method is not compatible with production of food ingredients, because TCA is not allowed in food products. Furthermore, the method includes gel filtration, which is not suitable for large-scale production.

Bayless K J, Davis G E, Meininger G A. 1997. Protein Expression and Purification 9, 309-314, Isolation and biological properties of osteopontin from bovine milk describes a method including ion-exchange and two steps of hydrophobic chromatography on phenyl-separose columns. The complexity of the process, and especially the hydrophobic chromatography makes the method inapplicable for large-scale purification of osteopontin.

Senger D R, Peruzzi C A, Papadopoulos A, Tenen D G. 1989. Biochimica et Biophysica Acta 996, 43-48. Purification of a human milk protein closely similar to tumor-secreted phosphoproteins and osteopontin proposes a purification method. The purification method described for human milk involves barium citrate affinity as well as reverse phase HPLC chromatography, which makes it inapplicable for large-scale purification.

The present invention solves the above problems. The invention discloses a process for large-scale purification or isolation of osteopontin from bovine milk (and milk from other domesticated milk producing mammals e.g. goat, sheep, buffalo, lama, camel, etc.). Milk osteopontin is highly preferred because it occurs naturally in milk from domestic animals. According to the invention osteopontin is isolated by techniques approved for dairy foods production. This food-grade osteopontin can therefore be used as an ingredient in food products for human consumption without any risks.

The present invention proposes a process for isolation of osteopontin from milk, wherein a milk material containing osteopontin and a material containing calcium are mixed and pH is adjusted to keep osteopontin in solution while precipitating other milk constituents or to aggregate or bind osteopontin while removing other soluble constituents.

The process can be performed in one or more steps. It is also possible to combine the steps of keeping osteopontin in solution and binding or aggregating it.

In the process of the invention the raw material is preferably based on milk containing osteopontin. Whey is a good raw material, since the casein proteins contained therein have been removed. Especially whey originating from chemical acidifying of milk is suitable, because its osteopontin is intact. On the other hand, the osteopontin contained in cheese whey can be partially hydrolysed. However, it is not yet known whether this reduces or completely destroys the properties of osteopontin.

Separation of osteopontin from denatured and precipitated protein can be performed by microfiltration or centrifugation as normally performed in the dairy industry.

The pore size can be from 0.1 to 1.4 µm. Ceramic filters are especially well suited owing to mechanical stability and long life. The separation can take place at temperatures from 10 to 80° C. 50-55° C. are especially well suited owing to great capacity and stable bacteriological conditions.

All types of anion exchangers can be used. Here a DEAE Sepharose fast flow exchanger is used. During the ion exchange pH can vary from approx. 3 to approx. 6.

The steps involving (A) solution or solubilization of osteopontin or (B) aggregation or binding of osteopontin can be combined in one process. The product streams can be treated in different ways before and/or after these steps to concentrate, separate, dry or perform other processes commonly used in the diary industry. Thus e.g. microfiltration can be used. The person skilled in the diary art will easily determine a proper filter, cf. e.g. Tetra Paks "Dairy processing Handbook" (1995), pp 123-132.

Normally it is preferred to concentrate whey before starting the process of the invention to reduce the amount of water to treat. For preconcentration of whey any conventional ultrafiltration system can be used: plate and frame; hollow fibre, tubular, ceramic and spiral, etc. Spiral systems are especially well suited from an economic point of view for the time being. Any membrane which does not allow osteopontin to pass through the membrane is suitable. The pore size of such membranes is 20,000 D or less. Suitable membranes are e.g. Koch HFK131, Desal PW or similar membranes.

The soluble Ca source can be any soluble calcium compound, such as calcium hydroxide, calcium chloride or calcium acetate. Calcium nitrite and calcium nitrate is also useable, but will normally not be recommended, if osteopontin is to be used in the food industry.

To aggregate or bind osteopontin to an insoluble Ca source use can be made of $Ca_3PO_4$ or other insoluble Ca source. pH adjustment to precipitate calcium phosphate or another insoluble salt with osteopontin can be within the range 6.0-8.5. The pH range 6.5-8.0 is particularly well suited. Especially, pH about 7.0 is suitable. Any base can be used; organic as well as inorganic, as pH adjustment agent in this process. Especially the bases NaOH, KOH, $Ca(OH)_2$ are suitable. Especially NaOH is suitable.

pH adjustment to keep osteopontin in solution is 3.5 to 5.0, preferably 4.0-4.6. pH 4.2 is most preferred. For the pH adjustment any organic or inorganic acid can be used. Hydrochloric acid is especially suitable owing to strength and price. If the milk starting material containing osteopontin also contains natural calcium from the milk less calcium is to be added or no calcium at all. Also, use of $Ca(OH)_2$ for pH adjustment can minimise the amount of other Ca source. Normally a suitable amount will be one where the concentration of calcium in the solution is 0.2%. There is no lower limit, but less than about 0.05% per protein % will give a reduced yield of osteopontin. 0.1% of calcium will be effective, but the yield of osteopontin is reduced compared to using 0.2% of calcium. Concentrations of calcium up to 0.4% have been tried. However, only little increase is obtained by concentrations above 0.2%. Therefore, 0.2% is preferred, but also 0.3% could be used.

Separation of precipitated calcium phosphate or another solid Ca source containing osteopontin can be separated from the rest by any usual method, such as microfiltration or centrifugation. The pore size can be from 0.1 to 1.4 µm. Ceramic filters are especially well suited owing to mechanical stability and long life. The separation can take place at temperatures from 10 to 80° C. 50-55° C. are especially well suited owing to great capacity and stable bacteriological conditions.

For the separation of osteopontin from dissolved calcium salt any ultrafiltration system can be used: plate and frame; hollow fibre, tubular, ceramic and spiral, etc. Spiral systems are especially well suited from an economic point of view. Any membrane which does not allow osteopontin to pass through the membrane can be used. The nominal pore size of such membranes is typically 20,000 D or less. Suitable membranes are e.g. Koch HFK328, Desal PV or similar membranes. All types of anion exchangers can be used. Here DEAE Sepharose fast flow exchanger is used.

During the ion exchange pH can vary from approx. 3 to approx. 6.

Germ filtration of whey protein concentrate, WPC, retentate before the pH adjustment to 7.0 in order to precipitate $Ca_3(PO_4)_2$ or another solid with oseopontin produces a purer aggregate, which will also give a purer product for further processing in the processes and thus also a little purer osteopontin products.

The following examples are intended to illustrate but not limit the present invention.

EXAMPLE 1

1000 kg of casein whey with pH 4.55, 0.53% protein, approximately 20 ppm osteopontin (0.002%), and 4.50% dry matter are concentrated in a spiral ultrafiltration plant with membranes having a nominal pore size so that the proteins do not pass through the membrane. Typical nominal pore size is 10,000 D. The temperature during the filtration is 50° C. and the mean pressure is 3.5 bars. Concentration is carried on until 900 kg of permeate, which do not contain osteopontin, are removed. During the concentration mean flux is 45.6 litres/m$^2$/h. 100 kg of retentate with pH 4.55, 3.86% protein, approx. 200 ppm osteopontin (0.02%), and 10.3% dry matter are left.

The 100 kg of retentate are pasteurized at 68° C. for 15 sec and cooled to 50° C. Hereafter pH is adjusted to 7.0 with 6% NaOH.

After being allowed to stand for 2 hours, microfiltration is performed on 0.1.4 µm ceramic membranes at 50° C. with a mean pressure of 4.0 bars. Diafiltration is carried out with 50° C. hot demineralized water pH adjusted to 7.0 until the conductivity in the permeate is below 100 µS. During the entire filtration the mean flux is 310 litres/m$^2$/h.

20,0 kg of retentate from the microfiltration are collected and cooled to 8° C. in ice water, with pH 7.0, 0.58% protein, approx. 1000 ppm osteopontin (0.1%), and 4.1% dry matter. The retentate is spray dried in a NIRO tower drier and 0.7 kg of powder with 13.6% protein, approx. 2.3% osteopontin, and 96.4% dry matter is obtained. The dry matter consists of 80% ashes, 27% calcium and 13.8% phosphorus.

EXAMPLE 2

2000 kg of casein whey with pH 4.55, 0.55% protein, approximately 20 ppm osteopontin (0.002%), and 4.53% dry matter are concentrated in a spiral UF plant with membranes having a nominal pore size so that the proteins do not pass through the membrane. Typical pore size is 10,000D. The temperature during the filtration is 12° C. and the mean pressure is 3.5 bars. Concentration is carried on until 1800 kg of permeate, which do not contain osteopontin, are removed. During the concentration mean flux is 27.6 litres/m$^2$/h. 200 kg of retentate with pH 4.55, 3.97% protein, approx. 200 ppm osteopontin (0.02%), and 10.4% dry matter are left.

The 200 kg of retentate are pasteurized at 68° C. for 15 sec and cooled to 50° C. Hereafter pH is adjusted to 7.0 with 6% NaOH.

After being allowed to stand for 30 min, microfiltration is carried out on 0.2 m$^2$ 1.4 µm ceramic membranes at 50° C. with a mean pressure of 4.0 bars. Diafiltration is performed with 50° C. hot demineralized water pH adjusted to 7.0 until the conductivity in the permeate is below 100 µS. During the entire filtration the mean flux is 310 litres/m$^2$/h. 20.0 kg of retentate from the microfiltration are collected and cooled to 8° C. in ice water, with pH 7.0, 1.25% protein, approx. 2,000 ppm osteopontin (0.2%), and 8.3% dry matter.

The retentate is pH adjusted to 3.0 with 28% hydrochloric acid, which produces an almost clear solution.

This pH 3.0 adjusted solution is ultrafiltered at 10° C. and the mean pressure 4.0 bars on a membrane with a cut-off value of 5,000D. The retentate is diafiltered with demineralized water until the conductivity in the permeate is below 0.1 μS. During the entire filtration the mean flux is 17.8 litres/m$^2$/h. 10 kg of retentate with 2.42% protein, approx. 4,000 ppm osteopontin (0.4%), and 2.6% dry matter are collected.

The retentate is spray dried in a NIRO tower drier and 0.2 kg of powder with 89.6% protein, approx. 14.8% osteopontin, and 96.4% dry matter is obtained.

EXAMPLE 3

1000 kg of preconcentrated casein whey with pH 4.55, 3.76% protein, approx. 200 ppm osteopontin (0.02%), and 10.3% dry matter are pasteurised at 67° C. for 15 sec and cooled to 50° C. Hereafter pH is adjusted to 7.0 with 6% NaOH.

After being allowed to stand for 60 min, microfiltration is carried out on 2.8 m$^2$ 1.4 μm ceramic membranes at 50° C. with a mean pressure of 4.0 bars. Diafiltration is performed with 50° C. hot demineralized water pH adjusted to 7.0 until the conductivity in the permeate is below 100 μS. During the whole filtration the mean flux is 325 litres/m$^2$/h.

100 kg of retentate from the microfiltration with pH 7.0, 1.22% protein, approx. 2,000 ppm osteopontin (0.2%), and 8.3% dry matter are collected and cooled to 5° C. on a plate heat exchanger.

The retentate is pH adjusted to 3.0 with 28% hydrochloric acid, which produces an almost clear solution. This pH 3.0 adjusted solution is ultrafiltered at 10° C. and the mean pressure 4.0 bars on a membrane with a cut-off value of 5,000D. The retentate is diafiltered with demineralized water until the conductivity in the permeate is below 100 μS. Then diafiltration is performed with 0.45 M KH$_2$PO$_4$ with pH=4.5 until pH is 4.5 in the retentate. During the entire filtration the mean flux is 15.9 litres/m$^2$/h. 10 kg retentate with 12.1% protein, approx. 20,000 ppm osteopontin (2.0%), and 13.4% dry matter are collected.

The retentate is pumped through a column with an anion exchanger which is equilibrated with 0.45 M KH$_2$PO$_4$ with pH=4.5. Thus osteopontin is bound to the column while the greater part of other whey proteins is not bound. The column is washed with 0.45 M KH$_2$PO$_4$ with pH=4.5 until the absorption at 280 nm is 0.

Osteopontin is eluted from the anion exchanger with 0.7 M KH$_2$PO$_4$ with pH=4.5 until the absorption at 280 nm is 0 and 50 litres of eluate containing 500 g protein, of which 40% is osteopontin, are collected. The eluate is concentrated and diafiltered to remove salts on ultrafiltration membranes having a pore size of 5,000D, at 10° C. and the mean pressure 4.0 bars. 5 kg of retentate with 10.7% dry matter, approx. 4% osteopontin, and 9.6% protein are collected. The retentate is spray dried in a NIRO tower drier and 0.5 kg of powder with 86.0% protein, approx. 36% osteopontin, and 95.8% dry matter is obtained.

EXAMPLE 4

1000 kg of casein whey with pH 4.56, 0.52% protein, approx. 20 ppm osteopontin (0.002%), and 4.50% dry matter are pasteurised at 71° C. for 15 s and cooled to 50° C. Hereafter pH is adjusted to 7.0 with 6% NaOH.

After being allowed to stand for 2 hours, microfiltration is performed on 1.4 m$^2$ 1.4 μm ceramic membranes at 50° C. with a mean pressure of 4.0 bars. Diafiltration is performed with 50° C. hot demineralized water pH adjusted to 7.0 until the conductivity in the permeate is below 100 μS. During the entire filtration the mean flux is 520 litres/m$^2$/h.

30.0 kg of retentate from the microfiltration are collected and cooled to 8° C. with ice water, with pH 7.0, 0.78% protein, approx. 670 ppm osteopontin (0.07%), and 16.1% dry matter. The retentate is spray dried in a NIRO tower drier and 4.5 kg of powder with 4.7% protein, approx. 0.4% osteopontin, and 96.4% dry matter are obtained. The dry matter consists of 85% ashes, 27% calcium and 13.8% phosphorus.

EXAMPLE 5

5000 kg of casein whey with pH 4.56, 0.51% protein, approx. 20 ppm osteopontin (0.002%), and 4.50% dry matter are pasteurised at 69° C. for 15 sec and cooled to 50° C. Hereafter pH is adjusted to 7.0 with 6% NaOH.

After being allowed to stand for 2 hours, microfiltration is performed on 1.4 m$^2$ 1.4 μm ceramic membranes at 50° C. with a mean pressure of 4.0 bars. Diafiltration is carried out with 50° C. hot demineralized water pH adjusted to 7.0 until the conductivity in the permeate is below 100 μS. During the entire filtration the mean flux is 550 litres/m$^2$/h.

150 kg of retentate from the microfiltration are collected and cooled to 8° C. in ice water, with pH 7.0, 0.73% protein, approx. 670 ppm osteopontin (0.07%), and 16.4% dry matter.

The retentate is pH adjusted to 3.0 with 28% hydrochloric acid, which produces an almost clear solution. This pH 3.0 adjusted solution is ultrafiltered at 10° C. and the mean pressure 4.0 bars on a membrane with a cut-off value of 10,000D. The retentate is diafiltered with demineralized water until the conductivity in the permeate is below 100 μS. During the entire filtration the mean flux is 25.3 litres/m$^2$/h. 10 kg of retentate with 11.0% protein, approx. 10,000 ppm osteopontin (1.0%), and 12.6% dry matter are collected.

The retentate is spray dried in a NIRO tower drier and 1.1 kg of powder with 83.8% protein, approx. 7.6% osteopontin, and 96.2% dry matter are obtained.

EXAMPLE 6

10,000 kg of casein whey with pH 4.56, 0.54% protein, approx. 20 ppm osteopontin (0.002%), and 4.50% dry matter are pasteurised at 69° C. for 15 sec and cooled to 50° C. Hereafter pH is adjusted to 7.0 with 6% NaOH.

After being allowed to stand for 2 hours, microfiltration is performed on 2.8 m$^2$ 1.4 μm ceramic membranes at 50° C. with a mean pressure of 4.0 bars. Diafiltration is carried out with 50° C. hot demineralized water pH adjusted to 7.0 until the conductivity in the permeate is below 100 μS. During the entire filtration the mean flux is 570 litres/m$^2$/h.

300 kg of retentate from the microfiltration are collected and cooled to 8° C. in ice water, with pH 7.0, 0.76% protein, approx. 670 ppm osteopontin (0.07%), and 16.3 dry matter.

The retentate is pH adjusted to 3.0 with 28% hydrochloric acid, which produces an almost clear solution. This pH 3.0 adjusted solution is ultrafiltered at 10° C. and the mean pressure 4.0 bars on a membrane with a cut-off value of 10,000D. The retentate is diafiltered with demineralized water until the conductivity in the permeate is below 100 μS.

During the entire filtration the mean flux is 24.6 litres/m$^2$/h. 20 kg of retentate with 10.8% protein, approx. 10,000 ppm osteopontin (1.0%), and 12.3% dry matter are collected.

The retentate is pumped through a column with an anion exchanger which is equilibrated with 0.45 M KH$_2$PO$_4$ with pH=4.5. The osteopontin is thus bound to the column, while the greater part of other whey proteins is not bound. The column is washed with 0.45 M KH$_2$PO$_4$ with pH=4.5 until the absorption at 280 nm is 0.

Osteopontin is eluted from the anion exchanger with 0.7 M KH$_2$PO$_4$ with pH=4.5 until the absorption at 280 nm is 0 and 50 litres of eluate containing 560 g of protein, of which 36% is osteopontin, are collected. The eluate is concentrated and diafiltered to remove salts on ultrafiltration membranes having a pore size of 5,000D, at 10° C. and the mean pressure 4.0 bars. 5 kg of retentate with 12.3% dry matter, approx. 4% osteopontin, and 11.2% protein are collected. The rententate is spray dried in a NIRO tower drier and 0.6 kg of powder with 87.6% protein, approx. 31% osteopontin, and 96.2% dry matter is obtained.

EXAMPLE 7

10,000 kg of casein whey with pH 4.53, 0.55% protein, approx. 20 ppm osteopontin (0.002%), and 4.50% dry matter are ultra-/diafiltered in a spiral UF plant with membranes having a nominal pore size so that the proteins do not pass through the membrane. Typical pore size is 20,000D. The temperature during the filtration is 15° C. and the mean pressure is 3.5 bars. Once the filtration is terminated, 152 kg of retentate with pH 4.54, 23.1% protein, approx. 1,300 ppm osteopontin (0.13%), and 28.7% dry matter are collected. During the concentration mean flux is 25.6 litres/m$^2$/h. The 152 kg of retentate are diluted with 722 kg of demineralized water so that the protein content is 4.0%. pH is adjusted to 7.4 with 6% NaOH. Then heat treatment is performed at 85° C. for 30 minutes and cooling to 8° C. is carried out. 6.4 kg of CaCl$_2$,2H$_2$O is added to the heat treated retentate, and pH is adjusted to 4.2 with 6% hydrochloric acid.

After being allowed to stand for at least 2 hours (or to the next day), heating to 50° C. is performed and microfiltration is carried out on 1.4 m$^2$ 0.8 μm ceramic membranes at 50° C. with a mean pressure of 4.0 bars. Diafiltration is carried out with 50° C. hot demineralized water pH adjusted to 4.2 until the conductivity in the permeate is below 100 μS. During the filtration the mean flux is 415 litres/m$^2$/h. A total of 2,000 litres of permeate having continuously being cooled to 8° C. over a plate heat exchanger (PVV), with pH 4.2, 0.16% protein, approx. 100 ppm osteopontin (0.01%), and 4.1% dry matter is collected.

The permeate from the microfiltation is pH adjusted to 6.6 with 6% NaOH and it is ultra/diafiltered in a spiral UF plant at 10° C. with a mean pressure of 4.0 bars until the conductivity in the permeate is below 500 μS. A filtration on membranes having a pore size of 5,000D is carried out. 40 kg of retentate with pH 6.5, 7.9% protein, approx. 5,000 ppm osteopontin (0.5%), and 9.6% dry matter is collected.

The retentate is spray dried in a NIRO tower drier and 3.5 kg of powder with 79.2% protein, approx. 5.0% osteopontin, and 96.2% dry matter is obtained.

EXAMPLE 8

200 kg of casein whey retentate with pH 4.55, 23.2% protein, approx. 1,300 ppm osteopontin (0.13%), and 29.1% dry matter are diluted with 1,000 kg of demineralized water and pH is adjusted to 7.4 with 6% NaOH. Then heat treatment is carried out at 85° C. for 30 min and cooling to 8° C. is performed. 8.8 kg of CaCl$_2$, 2H$_2$O are added to the heat treated retentate; and pH is adjusted to 4.1 with 6% hydrochloric acid.

After standing for at least 2 hours (or to the next day), heating to 50° C. is performed and microfiltration is carried out on 2.8 m$^2$ 0.8 μm ceramic membranes at 50° C. with a mean pressure of 4.0 bars. Diafiltration is performed with 50° C. hot demineralized water pH adjusted to 4.1 until the conductivity in the permeate is below 100 μS. During the entire filtration the mean flux is 445 iitres/m$^2$/h. A total of 2,800 litres of permeate having been cooled to 8° C. over a plate heat exchanger (PVV), with pH 4.1, 0.16% protein, approx. 100 ppm osteopontin (0.01%), and 4.0% dry matter is collected.

The permeate from the microfiltration is pH adjusted to 6.6 with 6% NaOH and it is ultra/diafiltered in a spiral UF plant at 10° C. with a mean pressure of 4.0 bars until the conductivity in the permeate is below 500 μS. A filtration is carried out on membranes having a pore size of 5,000D. 40 kg of retentate with pH 6.5, 11.2% protein, approx. 6,500 ppm osteopontin (0.65%), and 12.4% dry matter is collected.

The retentate is pumped through a column with an anion exchanger which is equilibrated with 0.45 M KH$_2$PO$_4$ with pH=4.5. Osteopontin is thus bound to the column, while the greater part of other proteins is not bound. The column is washed with 0.45 M KH$_2$PO$_4$ with pH=4.5 until the absorption at 280 nm is 0.

Osteopontin is eluted from the anion exchanger with 0.7 M KH$_2$PO$_4$ with pH=4.5 until the absorption at 280 nm is 0 and 50 l of eluate containing 500 g of protein, of which 50% is osteopontin, are collected. The eluate is concentrated and diafiltered to remove salts on ultrafiltration membranes having a pore size of 5,000D, at 10° C. and the mean pressure 4.0 bars. 5 kg of retentate with 10.7% dry matter, approx. 5% osteopontin, and 9.6% protein are collected. The retentate is spray dried in a NIRO tower drier and 0.5 kg of powder with 86.0% protein, approx. 45% osteopontin, and 95.8% dry matter is obtained.

The invention claimed is:

1. A process for purification of osteopontin from milk comprising mixing a milk material containing osteopontin and a material containing calcium and adjusting pH to keep osteopontin in solution while precipitating other milk constituents or adjusting pH to aggregate or bind osteopontin while removing other milk constituents in solution.

2. A process according to claim 1, wherein the milk material is mixed with a soluble calcium salt and pH is adjusted to an acid pH to keep the osteopontin in solution while precipitating other milk constituents.

3. A process according to claim 2, wherein pH is adjusted to pH 3.5 to 5.0.

4. A process according to claim 2, wherein pH is adjusted to pH 4.0 to 4.6.

5. A process according to claim 2, wherein pH is adjusted to pH about 4.2.

6. A process according to claim 2, wherein the soluble calcium source is calcium chloride.

7. A process according to claim 1, wherein the milk material is mixed with an insoluble calcium salt and pH is adjusted to a neutral to basic pH to bind or aggregate the osteopontin while precipitating it without precipitating the major part to the other milk constituents.

8. A process according to claim 7, wherein pH is adjusted to pH 6.0 to 8.5.

9. A process according to claim 7, wherein pH is adjusted to pH 6.5 to 8.0.

10. A process according to claim 7, wherein pH is adjusted to pH about 7.

11. A process according to claim 1, wherein the mixing and adjusting steps are carried out sequentially.

12. A process according to claim 7, wherein, in separate steps, a milk material containing osteopontin is mixed with an insoluble calcium salt and the pH is adjusted to a neutral or basic pH to bind or aggregate the osteopontin while precipitating it without precipitating the major part of the other milk constituents.

13. A process according to claim 1, wherein the milk material containing osteopontin is a whey product.

14. A process according to claim 1, wherein the milk material containing osteopontin is a concentrated whey product.

15. A process according to claim 1, wherein the milk material containing osteopontin is a whey product from chemical acidification of milk.

16. A process according to claim 2 or 7, wherein the milk material containing osteopontin and the material containing calcium are mixed so that the concentration of calcium in the mixture is about 0.05-0.3% based on protein weight %.

17. A process according to claim 16, wherein the milk material containing osteopontin and the material containing calcium are mixed so that the concentration of calcium in the mixture is about 0.2% based on protein weight %.

18. A process for purification of osteopontin from milk comprising adjusting the pH of a milk material containing osteopontin and calcium to keep osteopontin in solution while precipitating other milk constituents or to aggregate or bind osteopontin while removing other milk constituents in solution.

19. The process according to claim 18, wherein the pH is adjusted to pH 4.0 to 4.6 to keep the osteopontin in solution while precipitating other milk constituents.

20. The process according to claim 18, wherein the pH is adjusted to pH 6.5 to 8.0 to bind or aggregate the osteopontin while precipitating it without precipitating the major part of the other milk constituents.

* * * * *